US011492603B2

(12) United States Patent
Kagawa et al.

(10) Patent No.: US 11,492,603 B2
(45) Date of Patent: Nov. 8, 2022

(54) TRICHODERMA REESEI MUTANT AND PROTEIN PRODUCTION METHOD

(71) Applicant: Toray Industries, Inc., Tokyo (JP)

(72) Inventors: Yusuke Kagawa, Kamakura (JP); Haruka Saito, Kamakura (JP); Shingo Hiramatsu, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 76 days.

(21) Appl. No.: 17/040,593

(22) PCT Filed: Mar. 25, 2019

(86) PCT No.: PCT/JP2019/012505
§ 371 (c)(1),
(2) Date: Sep. 23, 2020

(87) PCT Pub. No.: WO2019/188980
PCT Pub. Date: Oct. 3, 2019

(65) Prior Publication Data

US 2021/0115487 A1 Apr. 22, 2021

(30) Foreign Application Priority Data

Mar. 26, 2018 (JP) ............................ JP2018-057616

(51) Int. Cl.

| | |
|---|---|
| ***C12N 9/00*** | (2006.01) |
| ***C12P 21/04*** | (2006.01) |
| ***C12P 19/00*** | (2006.01) |
| ***C12P 21/02*** | (2006.01) |
| ***C12N 15/09*** | (2006.01) |
| *C12N 1/14* | (2006.01) |

(52) U.S. Cl.
CPC ............... *C12N 9/00* (2013.01); *C12N 15/09* (2013.01); *C12P 19/00* (2013.01); *C12P 21/02* (2013.01); *C12N 1/14* (2013.01); *C12Y 302/01004* (2013.01)

(58) Field of Classification Search
CPC .. C12N 15/09; C12N 1/14; C12N 9/00; C12P 21/02; C12P 19/00
See application file for complete search history.

(56) References Cited

U.S. PATENT DOCUMENTS

| | | | |
|---|---|---|---|
| 2018/0216121 A1 | 8/2018 | Arai et al. | |
| 2019/0169239 A1 | 6/2019 | Shibata et al. | |
| 2021/0388410 A1 | 12/2021 | Kagawa et al. | |

FOREIGN PATENT DOCUMENTS

| | | | |
|---|---|---|---|
| EP | 3 805 365 | | 4/2021 |
| EP | 3 831 929 | | 6/2021 |
| EP | 3 845 630 | | 7/2021 |
| EP | 3 845 631 | | 7/2021 |
| JP | 2009-50247 | * | 3/2009 |
| JP | 2017-29013 | | 2/2017 |
| JP | 2018-19622 | | 2/2018 |
| WO | 2020/075787 | | 4/2020 |
| WO | 2020/075788 | | 4/2020 |

OTHER PUBLICATIONS

Harashima. English translation of Abstract of JP 2009050247. retrived on Feb. 1, 2022.*
Studer. Residue mutations and their impact on protein structure and function: detecting beneficial and pathogenic changes. Biochem. J. (2013) 449, 581-594.*
Juliano de Oliveira Porciuncula et al., "Single Nucleotide Polymorphism Analysis of a *Trichoderma reesei* Hyper-Cellulolytic Mutant Developed in Japan," Bioscience, Biotechnology, and Biochemistry, 2013, vol. 77, Issue 3, pp. 534-543.
Predicted protein [Trichoderma reesei QM6a], Database GenBank, EGR50654, [online], Jul. 25, 2016, [retrieved on May 29, 2019], Retrieved from the Internet: <https://www.ncbi.nlm.nih.gov/protein/EGR50654>.
Henri Durand et al., "Genetic improvement of *Trichoderma reesei* for large scale cellulase production," Enzyme. Microbiol. Technol., vol. 10, Issue 6, Jun. 1988, pp. 341-346 (Abstract).
B.J. Gallo etal., "Cellulase production by a new mutant strain of Trichoderma reesei MCG77,"Biotechnol. Bioeng. Symp., vol. 8, (1978) p. 89 (Abstract).
A.L. Allen et al., "Cellulase production in continuous and fed-batch culture by Trichoderma reesei MCG80," Biotechnol. Bioeng., vol. 12, 1982, pp. 451-459 (Abstract).
Assen Marintchev et al., "elF4G and CBP80 Share a Common Origin and Similar Domain Organization: Implications for the Structure and Function of elF4G±," Biochem., vol. 44, 2005, pp. 12265-12272 (Abstract).
Extended European Search Report of counterpart European Patent Application No. 19776489.7 dated Nov. 11, 2021.
Koike, H. et al., "Comparative Genomics Analysis of Trichoderma reesei Strains", *Industrial Biotechnology*, vol. 9, No. 6, pp. 352-367, Dec. 1, 2013.
Li, W.C, et al., "Trichoderma reesei complete genome sequence, repeat-induced point mutation, and partitioning of CAZyme gene clusters", *Biotechnology for Biofuels*, vol. 10, No. 1, p. 170, Jul. 3, 2017.
Notification of Substantive Examination Result dated May 12, 2022, of counterpart Indonesian Patent Application No. P00202006962, along with an English translation.

* cited by examiner

*Primary Examiner* — Yong D Pak
(74) *Attorney, Agent, or Firm* — DLA Piper LLP (US)

(57) ABSTRACT

A *Trichoderma reesei* mutant strain has a function of a polypeptide consisting of the amino acid sequence represented by SEQ ID NO: 2 is reduced. A method of producing a protein includes a step of cultivating the *Tricho-derma reesei* mutant strain, and a method of producing a cellulase includes a step of cultivating the *Trichoderma reesei* mutant strain.

7 Claims, No Drawings

Specification includes a Sequence Listing.

SEQUENCE LISTING

```
<160> NUMBER OF SEQ ID NOS: 12

<210> SEQ ID NO 1
<211> LENGTH: 2580
<212> TYPE: DNA
<213> ORGANISM: Trichoderma reesei

<400> SEQUENCE: 1

atgccgcacc gcgagcgcgg caagcagcga gaaggcggcg actcgtaccg cccctcgagg     60

ccagcgcgtt cacgctcgcg ctcgcgatcg ccgcctcgcg cgccggtgcc cgtgcggacg    120

gaggaggaga agcaggcggc ggcaaaggcc gagtacgaga agctgctcaa catgcggtcg    180

ggcggcacgt acatcccgcc ggcgaggctg agggcgctgc aggcgcagat cacggacaag    240

agcagcaagg agtaccagcg gatggcgtgg gaggcgctca agaagagcat caacggcctg    300

atcaacaagg tcaacacggc caacatcaag cacattgtgc ccgagctgtt tggcgagaac    360

ctggtgcgcg gccgcggcct cttctgccgc tccatcatga aggcccaggc cgccagtttg    420

cccttcacgc ccatctacgc cgccatggcc gccattgtca acaccaagct gccgcaggtc    480

ggcgagctgc tggtcaagcg cctcatcatg cagttccgca agggcttcaa gcgcaacgac    540

aaggccgtct gtctgtcgtc gaccaccttc ctcgcccacc tcatcaacca gcaggtgcag    600

cacgagatgc tggccggcca gatcctgctg ctgctgctgc acaagccgac cgacgacagc    660

gtcgagattg ccgtgggctt ctgcaaggag gttggccagt acctcgagga gatgcagcct    720

gccatttcca tggccgtctt cgaccagttc cgcaacatcc tccacgagtc cgacattgac    780

aagcgaacgc agtacatgat tgaggtgctc ttccagatca ggaaggacaa gttcaaggat    840

cacccggcca tcaaggagga gctggacttg gtggaggagg aggaccagat cacgcacaag    900

gtggagcttg atggcgagat tgatgtgcag gacggactca acatcttcaa gtacgacccg    960

gagtgggagg agcatgagga ggcatacaag aggctcaagg cggagattct gggcgaagcc   1020

agcgatgacg aggagggcga cgaggacgag gacgaggacg agagctccga agatgaagaa   1080

aacgaagaga caaaggccat ggagatcaag gaccagtcta acgccgactt ggtcaaccta   1140

cggaggacca tctacctcac catcatgtcg agcgccgacc cagaggaagc agttcacaag   1200

ctgatgaaga tcaacctgcc cgtcggccag gaacccgagc tgccctcgat gattgtcgag   1260

tgttgctcgc aggagaagac gtacaccaag ttctttggct tgatcggcga gcgtttcgcc   1320

aagatcaatc ggctgtggtg cgacctcttt gagcaggcct ttgtcaagta ctacgagacg   1380

atccaccgat acgaaaacaa caagctgcgg aacattgcca tgctgtttgg ccacatgttt   1440

gcttccgacg ctctgggctg gcactgcctt tccgtcattc acctcaacga ggaggagacc   1500

acgtcgagca gccgcatctt catcaagatt ctgttccagc acatttccga ggaaatcggc   1560

ctggctaagc tccgggcacg catgactgac gagacgctgc ggcccagcct cgaaggcctc   1620

ttccccagag agaaccctcg caacatccga ttctccatca actacttcac cagcatcggc   1680

atgggtgtac tgaccgagga gatgcgagag cacctcatga acatgcccaa gcctgcgctg   1740

cccgcccctg ctgctcagga ccgctcggat acggactccg tctcgagcta ttcgtcttac   1800

actcactcat catactcttc ccgctcgcgc tcacggtccc gatctgtggg tcgtcggagc   1860
```

```
ggcggtcgag gccgatcgct ttcccgaact ccgcctcgac gtggcgcaag gagccgatcc   1920

tactctgacg actcacggtc accgtcgcgg tcaagatcac gatcccgctc cgattccgtc   1980

tctactcgtg ggcgaaggcg agcgtcgtac tcggccagtc ctccccggcg tggtggccgt   2040

cgggttgcca gcagaagccg aagctactcg tcgggctcct cacggtctcc gccaccacgg   2100

aaccgcggtc gcgcacgaag caactcgtat agttcctaca gccgctctcc atcttcttca   2160

ccacgacgcg gcagagacgc agactcggcc agcccgcctc cgcgaagggg tcgaccgcgc   2220

cagagcccac caggcggtcc cgcaggtcga aggaacagct cgtctgtcgg cagcggaggg   2280

ccccgcaaga agccccgacg ggacagccga tcgccgtctc gcgactattc gtcccggtcc   2340

ccgtctcggt cgccgtcgag atctcgatcg cctccgccgg ctgcgcgtgg ccgaaggggc   2400

tcttatacgc cgtcacgcag ccgcagcccg cctccgcgca gggtgaggga tggctcgccg   2460

ggtcgtctga ggggtgggag gtcgcctagt cctcctttgc cggtgaagag gaggcggtat   2520

gatagcgaga gtgtttctcg gtcgccgcct cctttgaagc gcgggagaag ggataactaa   2580
```

<210> SEQ ID NO 2
<211> LENGTH: 859
<212> TYPE: PRT
<213> ORGANISM: Trichoderma reesei

<400> SEQUENCE: 2

```
Met Pro His Arg Glu Arg Gly Lys Gln Arg Glu Gly Gly Asp Ser Tyr
1               5                   10                  15

Arg Pro Ser Arg Pro Ala Arg Ser Arg Ser Arg Ser Arg Ser Pro Pro
            20                  25                  30

Arg Ala Pro Val Pro Val Arg Thr Glu Glu Glu Lys Gln Ala Ala Ala
        35                  40                  45

Lys Ala Glu Tyr Glu Lys Leu Leu Asn Met Arg Ser Gly Gly Thr Tyr
    50                  55                  60

Ile Pro Pro Ala Arg Leu Arg Ala Leu Gln Ala Gln Ile Thr Asp Lys
65                  70                  75                  80

Ser Ser Lys Glu Tyr Gln Arg Met Ala Trp Glu Ala Leu Lys Lys Ser
                85                  90                  95

Ile Asn Gly Leu Ile Asn Lys Val Asn Thr Ala Asn Ile Lys His Ile
            100                 105                 110

Val Pro Glu Leu Phe Gly Glu Asn Leu Val Arg Gly Arg Gly Leu Phe
        115                 120                 125

Cys Arg Ser Ile Met Lys Ala Gln Ala Ala Ser Leu Pro Phe Thr Pro
    130                 135                 140

Ile Tyr Ala Ala Met Ala Ala Ile Val Asn Thr Lys Leu Pro Gln Val
145                 150                 155                 160

Gly Glu Leu Leu Val Lys Arg Leu Ile Met Gln Phe Arg Lys Gly Phe
                165                 170                 175

Lys Arg Asn Asp Lys Ala Val Cys Leu Ser Ser Thr Thr Phe Leu Ala
            180                 185                 190

His Leu Ile Asn Gln Gln Val Gln His Glu Met Leu Ala Gly Gln Ile
        195                 200                 205

Leu Leu Leu Leu Leu His Lys Pro Thr Asp Asp Ser Val Glu Ile Ala
    210                 215                 220

Val Gly Phe Cys Lys Glu Val Gly Gln Tyr Leu Glu Glu Met Gln Pro
225                 230                 235                 240

Ala Ile Ser Met Ala Val Phe Asp Gln Phe Arg Asn Ile Leu His Glu
```

-continued

```
                245                 250                 255

Ser Asp Ile Asp Lys Arg Thr Gln Tyr Met Ile Glu Val Leu Phe Gln
            260                 265                 270

Ile Arg Lys Asp Lys Phe Lys Asp His Pro Ala Ile Lys Glu Glu Leu
        275                 280                 285

Asp Leu Val Glu Glu Glu Asp Gln Ile Thr His Lys Val Glu Leu Asp
    290                 295                 300

Gly Glu Ile Asp Val Gln Asp Gly Leu Asn Ile Phe Lys Tyr Asp Pro
305                 310                 315                 320

Glu Trp Glu Glu His Glu Glu Ala Tyr Lys Arg Leu Lys Ala Glu Ile
                325                 330                 335

Leu Gly Glu Ala Ser Asp Asp Glu Glu Gly Asp Glu Asp Glu Asp Glu
            340                 345                 350

Asp Glu Ser Ser Glu Asp Glu Glu Asn Glu Glu Thr Lys Ala Met Glu
        355                 360                 365

Ile Lys Asp Gln Ser Asn Ala Asp Leu Val Asn Leu Arg Arg Thr Ile
    370                 375                 380

Tyr Leu Thr Ile Met Ser Ser Ala Asp Pro Glu Glu Ala Val His Lys
385                 390                 395                 400

Leu Met Lys Ile Asn Leu Pro Val Gly Gln Glu Pro Glu Leu Pro Ser
                405                 410                 415

Met Ile Val Glu Cys Cys Ser Gln Glu Lys Thr Tyr Thr Lys Phe Phe
            420                 425                 430

Gly Leu Ile Gly Glu Arg Phe Ala Lys Ile Asn Arg Leu Trp Cys Asp
        435                 440                 445

Leu Phe Glu Gln Ala Phe Val Lys Tyr Tyr Glu Thr Ile His Arg Tyr
    450                 455                 460

Glu Asn Asn Lys Leu Arg Asn Ile Ala Met Leu Phe Gly His Met Phe
465                 470                 475                 480

Ala Ser Asp Ala Leu Gly Trp His Cys Leu Ser Val Ile His Leu Asn
                485                 490                 495

Glu Glu Glu Thr Thr Ser Ser Ser Arg Ile Phe Ile Lys Ile Leu Phe
            500                 505                 510

Gln His Ile Ser Glu Glu Ile Gly Leu Ala Lys Leu Arg Ala Arg Met
        515                 520                 525

Thr Asp Glu Thr Leu Arg Pro Ser Leu Glu Gly Leu Phe Pro Arg Glu
    530                 535                 540

Asn Pro Arg Asn Ile Arg Phe Ser Ile Asn Tyr Phe Thr Ser Ile Gly
545                 550                 555                 560

Met Gly Val Leu Thr Glu Glu Met Arg Glu His Leu Met Asn Met Pro
                565                 570                 575

Lys Pro Ala Leu Pro Ala Pro Ala Ala Gln Asp Arg Ser Asp Thr Asp
            580                 585                 590

Ser Val Ser Ser Tyr Ser Ser Tyr Thr His Ser Ser Tyr Ser Ser Arg
        595                 600                 605

Ser Arg Ser Arg Ser Arg Ser Val Gly Arg Arg Ser Gly Gly Arg Gly
    610                 615                 620

Arg Ser Leu Ser Arg Thr Pro Pro Arg Arg Gly Ala Arg Ser Arg Ser
625                 630                 635                 640

Tyr Ser Asp Asp Ser Arg Ser Pro Ser Arg Ser Arg Ser Arg Ser Arg
                645                 650                 655

Ser Asp Ser Val Ser Thr Arg Gly Arg Arg Arg Ala Ser Tyr Ser Ala
            660                 665                 670
```

```
Ser Pro Pro Arg Arg Gly Gly Arg Arg Val Ala Ser Arg Ser Arg Ser
        675                 680                 685

Tyr Ser Ser Gly Ser Ser Arg Ser Pro Pro Pro Arg Asn Arg Gly Arg
    690                 695                 700

Ala Arg Ser Asn Ser Tyr Ser Ser Tyr Ser Arg Ser Pro Ser Ser Ser
705                 710                 715                 720

Pro Arg Arg Gly Arg Asp Ala Asp Ser Ala Ser Pro Pro Pro Arg Arg
                725                 730                 735

Gly Arg Pro Arg Gln Ser Pro Pro Gly Gly Pro Ala Gly Arg Arg Asn
            740                 745                 750

Ser Ser Ser Val Gly Ser Gly Gly Pro Arg Lys Lys Pro Arg Arg Asp
        755                 760                 765

Ser Arg Ser Pro Ser Arg Asp Tyr Ser Ser Arg Ser Pro Ser Arg Ser
    770                 775                 780

Pro Ser Arg Ser Arg Ser Pro Pro Pro Ala Ala Arg Gly Arg Arg Gly
785                 790                 795                 800

Ser Tyr Thr Pro Ser Arg Ser Arg Ser Pro Pro Pro Arg Arg Val Arg
                805                 810                 815

Asp Gly Ser Pro Gly Arg Leu Arg Gly Gly Arg Ser Pro Ser Pro Pro
            820                 825                 830

Leu Pro Val Lys Arg Arg Arg Tyr Asp Ser Glu Ser Val Ser Arg Ser
        835                 840                 845

Pro Pro Pro Leu Lys Arg Gly Arg Arg Asp Asn
    850                 855
```

<210> SEQ ID NO 3
<211> LENGTH: 7801
<212> TYPE: DNA
<213> ORGANISM: Artificial Sequence
<220> FEATURE:
<223> OTHER INFORMATION: DNA fragment for transformation

<400> SEQUENCE: 3

```
taacttaagg cgcggattga gcccacgctg gcatgaagtt tagagggaaa cgcgccagag     60
gtgcctttca agtgagagcg aggttagggg gggcttggat tgggctggag gtacggcgtg    120
tggcgttgca gagtacatca atttgcgcag tgacggatag ggcggggtga ggtagagctt    180
tccgggagca gaggtactgc tgcttgaagc cgggctgctg tggcgtgctg taacttggcc    240
cgtgcacgct tttgccatct tttcctcgt ttcgttgctt cagccttagc aaaacccatc    300
cgccgccatc actcgattct gggtgacgac gacgaggcag gcgtttttta ttcttttcga    360
gcagagcatt gcctgtgtct cctctcccag ttcaaccctt tgaatccttg tcattgccgg    420
cccttgaccg cccatctcta cgactcgaac gacatatacc cttcccgtcc atccagatcg    480
cgacacacac gatggcggcc gtcgtcgaca tgccgcaccg cgagcgcggc aagcagcgag    540
aaggcggcga ctcgtaccgc ccctcgaggc cagcgcgttc acgctcgcgc tcgcgatcgc    600
cgcctcgcgc gccggtgccc gtgcggacgg aggaggagaa gcaggcggcg gcaaaggccg    660
agtacgagaa gctgctcaac atgcggtcgg gcggcacgta catcccgccg gcgaggctga    720
gggcgctgca ggcgcagatc acggacaaga gcagcaagga gtaccagcgg atggcgtggg    780
aggcgctcaa gaagagcatc aacggcctga tcaacaaggt caacacggcc aacatcaagc    840
acattgtgcc cgagctgttt ggcgagaacc tggtgcgcgg ccgcggcctc ttctgccgct    900
ccatcatgaa ggcccaggcc gccagtttgc ccttcacgcc catctacgcc gccatggccg    960
```

-continued

```
ccattgtcaa caccaagctg ccgcaggtcg gcgagctgct ggtcaagcgc ctcatcatgc   1020
agttccgcaa gggcttcaag cgcaacgaca aggccgtctg tctgtcgtcg accaccttcc   1080
tcgcccacct catcaaccag caggtgcagc acgagatgct ggccggccag atcctgctgc   1140
tgctgctgca caagccgacc gacgacagcg tcgagattgc cgtgggcttc tgcaaggagg   1200
ttggccagta cctcgaggag atgcagcctg ccatttccat ggccgtcttc gaccagttcc   1260
gcaacatcct ccacgagtcc gacattgaca agcgaacgca gtacatgatt gaggtgctct   1320
tccagatcag gaaggacaag ttcaaggatc acccggccat caaggaggag ctggacttgg   1380
tggaggagga ggaccagatc acgcacaagg tggagcttga tggcgagatt gatgtgcagg   1440
acggactcaa catcttcaag tacgacccgg agtgggagga gcatgaggag gcatacaaga   1500
ggctcaaggc ggagattctg ggcgaagcca gcgatgacga ggagggcgac gaggacgagg   1560
acgagagctc cgaagatgaa gaaaacgaag agacaaaggc catggagatc aaggaccagt   1620
ctaacgccga cttggtcaac ctacggagga ccatctacct caccatcatg tcgagcgccg   1680
acccagagga agcagttcac aagctgatga agatcaacct gcccgtcggc caggaacccg   1740
agctgccctc gatgattgtc gagtgttgct cgcaggagaa gacgtacacc aagttctttg   1800
gcttgatcgg cgagcgtttc gccaagatca atcggctgtg gtgcgacctc tttgagcagg   1860
cctttgtcaa gtactacgag acgatccacc gatacgaaaa caacaagctg cggaacattg   1920
ccatgctgtt tggccacatg tttgcttccg acgctctggg ctggcactgc ctttccgtca   1980
ttcacctcaa cgaggaggag accacgtcga gcagccgcat cttcatcaag attctgttcc   2040
agcacatttc cgaggaaatc ggcctggcta agctccgggc acgcatgact gacgagacgc   2100
tgcggcccag cctcgaaggc ctcttcccca gagagaaccc tcgcaacatc cgattctcca   2160
tcaactactt caccagcatc ggcatgggtg tactgaccga ggagatgcga gagcacctca   2220
tgaacatgcc caagcctgcg ctgcccgccc ctgctgctca ggaccgctcg gatacggact   2280
ccgtctcgag ctattcgtct tacactcact catcatactc ttcccgctcg cgctcacggt   2340
cccgatctgt gggtcgtcgg agcggcggtc gaggccgatc gctttcccga actccgcctc   2400
gacgtggcgc aaggagccga tcctactctg acgactcacg gtcaccgtcg cggtcaagat   2460
cacgatcccg ctccgattcc gtctctactc gtgggcgaag gcgagcgtcg tactcggcca   2520
gtcctccccg gcgtggtggc cgtcgggttg ccagcagaag ccgaagctac tcgtcgggct   2580
cctcacggtc tccgccacca cggaaccgcg gtcgcgcacg aagcaactcg tatagttcct   2640
acagccgctc tccatcttct tcaccacgac gcggcagaga cgcagactcg gccagcccgc   2700
ctccgcgaag ggtcgaccg cgccagagcc caccaggcgg tcccgcaggt cgaaggaaca    2760
gctcgtctgt cggcagcgga gggccccgca agaagccccg acgggacagc cgatcgccgt   2820
ctcgcgacta ttcgtcccgg tccccgtctc ggtcgccgtc gagatctcga tcgcctccgc   2880
cggctgcgcg tggccgaagg ggctcttata cgccgtcacg cagccgcagc ccgcctccgc   2940
gcagggtgag ggatggctcg ccgggtcgtc tgaggggtgg gaggtcgcct agtcctcctt   3000
tgccggtgaa gaggaggcgg tatgatagcg agagtgtttc tcggtcgccg cctcctttga   3060
agcgcgggag aagggataac taaaccttta ccttttgaac gatgaattgt tcctcttgct   3120
tagattgaaa cggttaagcg gagtggaatt gggtgggatg ggaaaacgtg taatagattg   3180
gttggtaccg cggccgccta gtcatcattg gataggcaga ttactcagcc tgaatgacat   3240
caacatgtta cccatgatac aataggtcac acaaacaagc gctaagatgc acttggtatg   3300
acaagcccag tagtccgttt caaaagacct agatgatgaa ctacaacatg aggtgttgcc   3360
```

-continued

```
tcctgatcca gtccaactgc aaacgctgat gtatactcaa tcaagcctga tgtaaatgct   3420
gcgactcgat tcgctggata tgaagatcaa agagagctct gatgggtcca atatagccgg   3480
gttttgttag gacagtccac cacaccgata ttagaattgg tcaagcacct tatcatttca   3540
tagagattgc ggtttctaga tctacgccag gaccgagcaa gcccagatga gaaccgacgc   3600
agatttcctt ggcacctgtt gcttcagctg aatcctggca atacgagata cctgctttga   3660
atattttgaa tagctcgccc gctggagagc atcctgaatg caagtaacaa ccgtagaggc   3720
tgacacggca ggtgttgcta gggagcgtcg tgttctacaa ggccagacgt cttcgcggtt   3780
gatatatatg tatgtttgac tgcaggctgc tcagcgacga cagtcaagtt cgccctcgct   3840
gcttgtgcaa taatcgcagt ggggaagcca caccgtgact cccatctttc agtaaagctc   3900
tgttggtgtt tatcagcaat acacgtaatt taaactcgtt agcatggggc tgatagctta   3960
attaccgttt accagtgccg cggttctgca gctttccttg gcccgtaaaa ttcggcgaag   4020
ccagccaatc accagctagg caccagctaa accctataat tagtctctta tcaacaccat   4080
ccgctccccc gggatcaatg aggagaatga gggggatgcg gggctaaaga agcctacata   4140
accctcatgc caactcccag tttacactcg tcgagccaac atcctgacta taagctaaca   4200
cagaatgcct caatcctggg aagaactggc cgctgataag cgcgcccgcc tcgcaaaaac   4260
catccctgat gaatggaaag tccagacgct gcctgcggaa gacagcgtta ttgatttccc   4320
aaagaaatcg ggcatccttt cagaggccga actgaagatc acagaggcct ccgctgcaga   4380
tcttgtgtcc aagctggcgg ccggagagtt gacctcggtg gaagttacgc tagcattctg   4440
taaacgggca gcaatcgccc agcagttagt agggtcccct ctacctctca gggagatgta   4500
acaacgccac cttatgggac tatcaagctg acgctggctt ctgtgcagac aaactgcgcc   4560
cacgagttct tccctgacgc cgctctcgcg caggcaaggg aactcgatga atactacgca   4620
aagcacaaga gacccgttgg tccactccat ggcctcccca tctctctcaa agaccagctt   4680
cgagtcaagg tacaccgttg cccctaagtc gttagatgtc ccttttttgtc agctaacata   4740
tgccaccagg gctacgaaac atcaatgggc tacatctcat ggctaaacaa gtacgacgaa   4800
ggggactcgg ttctgacaac catgctccgc aaagccggtg ccgtcttcta cgtcaagacc   4860
tctgtcccgc agaccctgat ggtctgcgag acagtcaaca acatcatcgg gcgcaccgtc   4920
aacccacgca acaagaactg gtcgtgcggc ggcagttctg gtggtgaggg tgcgatcgtt   4980
gggattcgtg gtggcgtcat cggtgtagga acggatatcg gtggctcgat tcgagtgccg   5040
gccgcgttca acttcctgta cggtctaagg ccgagtcatg ggcggctgcc gtatgcaaag   5100
atggcgaaca gcatggaggg tcaggagacg gtgcacagcg ttgtcgggcc gattacgcac   5160
tctgttgagg gtgagtcctt cgcctcttcc ttcttttcct gctctatacc aggcctccac   5220
tgtcctcctt tcttgctttt tatactatat acgagaccgg cagtcactga tgaagtatgt   5280
tagacctccg cctcttcacc aaatccgtcc tcggtcagga gccatggaaa tacgactcca   5340
aggtcatccc catgccctgg cgccagtccg agtcggacat tattgcctcc aagatcaaga   5400
acggcgggct caatatcggc tactacaact tcgacggcaa tgtccttcca caccctccta   5460
tcctgcgcgg cgtggaaacc accgtcgccg cactcgccaa agccggtcac accgtgaccc   5520
cgtggacgcc atacaagcac gatttcggcc acgatctcat ctcccatatc tacgcggctg   5580
acggcagcgc cgacgtaatg cgcgatatca gtgcatccgg cgagccggcg attccaaata   5640
tcaaagacct actgaacccg aacatcaaag ctgttaacat gaacgagctc tgggacacgc   5700
```

-continued

```
atctccagaa gtggaattac cagatggagt accttgagaa atggcgggag gctgaagaaa   5760
aggccgggaa ggaactggac gccatcatcg cgccgattac gcctaccgct gcggtacggc   5820
atgaccagtt ccggtactat gggtatgcct ctgtgatcaa cctgctggat ttcacgagcg   5880
tggttgttcc ggttaccttt gcggataaga acatcgataa gaagaatgag agtttcaagg   5940
cggttagtga gcttgatgcc ctcgtgcagg aagagtatga tccggaggcg taccatgggg   6000
caccggttgc agtgcaggtt atcggacgga gactcagtga agagaggacg ttggcgattg   6060
cagaggaagt ggggaagttg ctgggaaatg tggtgactcc atagctaata agtgtcagat   6120
agcaatttgc acaagaaatc aataccagca actgtaaata agcgctgaag tgaccatgcc   6180
atgctacgaa agagcagaaa aaaacctgcc gtagaaccga agagatatga cacgcttcca   6240
tctctcaaag gaagaatccc ttcagggttg cgtttccagt ctagacgcgt gatgggtggg   6300
aatagggaat atttacttgg gttatgcgtc acatagtagc acccccttt tttgcccttc    6360
tttgatatca ttagcgattc aatacactaa ttacggacaa tcaccttggc ttctgtcatt   6420
ctatgtgctt gtgagcgaat ctactggttt gactgctgca cggtatatgt gagatcgtgg   6480
actgctaacc ccttctttct tcttggcaat ctatcgagga gccaaagaag aagacgcttc   6540
aatcttcaac gacgcactgt ctgcccccaat gcaggtccac agcaactcac ccgctttcaa  6600
agcaccccca accttgacaa gctgcttctc ccccggcaca acatcgaacc cgttgtcact   6660
cagctccaga ccctccacct cctcgaagac gaaccccttg acgggcttct ccgccgaaac   6720
gacgacttca tccccagcgg acgaaacctc aaacgcgata ccgcggtcag acaggtcgag   6780
gtacttgatg ggctcgggcc aagccgtgtc cgcagcgatg acggtgccag tcgcggcgtc   6840
cgtgatggtg gcatggacca cgtacggatc gtattcggcg aggggaaagg gcttggtgat   6900
gtcttccggg ttggggatgg atggcgggag cgtcttgccc tggaggatgt ccgtcgcgga   6960
gtttgcggcg gcgacgacgc gggagtgtag tatcggatcg acgacgtccc tgcctgtgcg   7020
gacggagatg aagcgcacga cgaggtccag cgcgacgggc tgggtgtcgc tgctgacgac   7080
ccagacgtca aaggttccct cgcgagcggc aagcgtgtgg tcgacctggc cggtgacgag   7140
gcccgagttc tcatcgaccc aggcccccgt ctgcgtccag tcgtgccacg tccggcagac   7200
gcccacgtcg acgcggcgca gggcccgcgc gatggcgtag tacgccggct tcttgacgag   7260
acggtagtcc accacggccc acgacatggt cggccagcag tcgttgagct gccacaccag   7320
cgcgccgccg caccgcctgg ccccgggctt cccccactgc cgccgccagg ccttgtacgc   7380
ggcgcgcatc gtctccgact gcacgacctg cgtcaggtgg gtgtacccgc cgaggtcgtg   7440
ccgcgggcgg aagttgtcga cgacgtagct catcatgcgg cgctcgtggc cgatggcctt   7500
gttgtgcgcg tcgagcacca tcgagcccgg gtacagctgg gctgggtcgc tggccatgcg   7560
gcgcgtggtg ctgagatggg ggtatgcttc catgccgaac tcgctgacga agcggccgcc   7620
catgttgacg gcctcttggt acttgttcat ggtcccatgc cagactgtgt ggagaggatg   7680
gtcagtggga tgttgcgtgt gagtgatttg tgtggaaatt gggggggggg gggggggggg   7740
gcttcttact gttccactga tggatatcgc caaccgttgg atctgccgtg actagtgcat   7800
g                                                                   7801
```

<210> SEQ ID NO 4
<211> LENGTH: 3186
<212> TYPE: DNA
<213> ORGANISM: Artificial Sequence
<220> FEATURE:
<223> OTHER INFORMATION: DNA fragment for transformation

<400> SEQUENCE: 4
cttaaggcgc ggattgagcc cacgctggca tgaagtttag agggaaacgc gccagaggtg 60
cctttcaagt gagagcgagg ttaggggggg cttggattgg gctggaggta cggcgtgtgg 120
cgttgcagag tacatcaatt tgcgcagtga cggatagggc ggggtgaggt agagctttcc 180
gggagcagag gtactgctgc ttgaagccgg gctgctgtgg cgtgctgtaa cttggcccgt 240
gcacgctttt gccatctttt tcctcgtttc gttgcttcag ccttagcaaa acccatccgc 300
cgccatcact cgattctggg tgacgacgac gaggcaggcg ttttttattc ttttcgagca 360
gagcattgcc tgtgtctcct ctcccagttc aaccctttga atccttgtca ttgccggccc 420
ttgaccgccc atctctacga ctcgaacgac atataccctt cccgtccatc cagatcgcga 480
cacacacgat ggcggccgtc gtcgacatgc cgcaccgcga gcgcggcaag cagcgagaag 540
gcggcgactc gtaccgcccc tcgaggccag cgcgttcacg ctcgcgctcg cgatcgccgc 600
ctcgcgcgcc ggtgcccgtg cggacggagg aggagaagca ggcggcggca aaggccgagt 660
acgagaagct gctcaacatg cggtcgggcg gcacgtacat cccgccggcg aggctgaggg 720
cgctgcaggc gcagatcacg gacaagagca gcaaggagta ccagcggatg gcgtgggagg 780
cgctcaagaa gagcatcaac ggcctgatca acaaggtcaa cacggccaac atcaagcaca 840
ttgtgcccga gctgtttggc gagaacctgg tgcgcggccg cggcctcttc tgccgctcca 900
tcatgaaggc ccaggccgcc agtttgccct tcacgcccat ctacgccgcc atggccgcca 960
ttgtcaacac caagctgccg caggtcggcg agctgctggt caagcgcctc atcatgcagt 1020
tccgcaaggg cttcaagcgc aacgacaagg ccgtctgtct gtcgtcgacc accttcctcg 1080
cccacctcat caaccagcag gtgcagcacg agatgctggc cggccagatc ctgctgctgc 1140
tgctgcacaa gccgaccgac gacagcgtcg agattgccgt gggcttctgc aaggaggttg 1200
gccagtacct cgaggagatg cagcctgcca tttccatggc cgtcttcgac cagttccgca 1260
acatcctcca cgagtccgac attgacaagc gaacgcagta catgattgag gtgctcttcc 1320
agatcaggaa ggacaagttc aaggatcacc cggccatcaa ggaggagctg gacttggtgg 1380
aggaggagga ccagatcacg cacaaggtgg agcttgatgg cgagattgat gtgcaggacg 1440
gactcaacat cttcaagtac gacccggagt gggaggagca tgaggaggca tacaagaggc 1500
tcaaggcgga gattctgggc gaagccagcg atgacgagga gggcgacgag gacgaggacg 1560
agagctccga agatgaagaa aacgaagaga caaaggccat ggagatcaag gaccagtcta 1620
acgccgactt ggtcaaccta cggaggacca tctacctcac catcatgtcg agcgccgacc 1680
cagaggaagc agttcacaag ctgatgaaga tcaacctgcc cgtcggccag gaacccgagc 1740
tgccctcgat gattgtcgag tgttgctcgc aggagaagac gtacaccaag ttctttggct 1800
tgatcggcga gcgtttcgcc aagatcaatc ggctgtggtg cgacctcttt gagcaggcct 1860
ttgtcaagta ctacgagacg atccaccgat acgaaaacaa caagctgcgg aacattgcca 1920
tgctgtttgg ccacatgttt gcttccgacg ctctgggctg gcactgcctt tccgtcattc 1980
acctcaacga ggaggagacc acgtcgagca gccgcatctt catcaagatt ctgttccagc 2040
acatttccga ggaaatcggc ctggctaagc tccgggcacg catgactgac gagacgctgc 2100
ggcccagcct cgaaggcctc ttccccagag agaaccctcg caacatccga ttctccatca 2160
actacttcac cagcatcggc atgggtgtac tgaccgagga gatgcgagag cacctcatga 2220
acatgcccaa gcctgcgctg cccgcccctg ctgctcagga ccgctcggat acggactccg 2280
tctcgagcta ttcgtcttac actcactcat catactcttc ccgctcgcgc tcacggtccc 2340
gatctgtggg tcgtcggagc ggcggtcgag gccgatcgct ttcccgaact ccgcctcgac 2400
gtggcgcaag gagccgatcc tactctgacg actcacggtc accgtcgcgg tcaagatcac 2460
gatcccgctc cgattccgtc tctactcgtg ggcgaaggcg agcgtcgtac tcggccagtc 2520
ctccccggcg tggtggccgt cgggttgcca gcagaagccg aagctactcg tcgggctcct 2580
cacggtctcc gccaccacgg aaccgcggtc gcgcacgaag caactcgtat agttcctaca 2640
gccgctctcc atcttcttca ccacgacgcg gcagagacgc agactcggcc agcccgcctc 2700
cgcgaagggg tcgaccgcgc cagagcccac caggcggtcc cgcaggtcga aggaacagct 2760
cgtctgtcgg cagcggaggg ccccgcaaga agccccgacg ggacagccga tcgccgtctc 2820
gcgactattc gtcccggtcc ccgtctcggt cgccgtcgag atctcgatcg cctccgccgg 2880
ctgcgcgtgg ccgaaggggc tcttatacgc cgtcacgcag ccgcagcccg cctccgcgca 2940
gggtgaggga tggctcgccg ggtcgtctga ggggtgggag gtcgcctagt cctcctttgc 3000
cggtgaagag gaggcggtat gatagcgaga gtgtttctcg gtcgccgcct cctttgaagc 3060
gcgggagaag ggataactaa acctttacct tttgaacgat gaattgttcc tcttgcttag 3120
attgaaacgg ttaagcggag tggaattggg tgggatggga aaacgtgtaa tagattggtt 3180
ggtacc 3186

<210> SEQ ID NO 5
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 5
atacgcgtga tgggtgggaa tagggaatat tta 33

<210> SEQ ID NO 6
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 6
atactagtca cggcagatcc aacggttggc gat 33

<210> SEQ ID NO 7
<211> LENGTH: 3516
<212> TYPE: DNA
<213> ORGANISM: Trichoderma reesei

<400> SEQUENCE: 7
agagaagaat cggcgatcga atgggcgtct ttggttcgtt gtttaaagga gcgtgggcgg 60
cgattctgga gttgattcaa gtaatagtga agaggtggaa gcttggattg ggtgaggcgc 120
ggattgagcc cacgctggca tgaagtttag agggaaacgc gccagaggtg cctttcaagt 180
gagagcgagg ttaggggggg cttggattgg gctggaggta cggcgtgtgg cgttgcagag 240
tacatcaatt tgcgcagtga cggatagggc ggggtgaggt agagctttcc gggagcagag 300
gtactgctgc ttgaagccgg gctgctgtgg cgtgctgtaa cttggcccgt gcacgctttt 360
gccatctttt tcctcgtttc gttgcttcag ccttagcaaa acccatccgc cgccatcact 420
cgattctggg tgacgacgac gaggcaggcg ttttttattc ttttcgagca gagcattgcc 480

-continued

```
tgtgtctcct ctcccagttc aacccctttga atccttgtca ttgccggccc ttgaccgccc    540
atctctacga ctcgaacgac atataccctt cccgtccatc cagatcgcga cacacacgat    600
ggcggccgtc gtcgacatgc cgcaccgcga gcgcggcaag cagcgagaag gcggcgactc    660
gtaccgcccc tcgaggccag cgcgttcacg ctcgcgctcg cgatcgccgc ctcgcgcgcc    720
ggtgcccgtg cggacggagg aggagaagca ggcggcggca aaggccgagt acgagaagct    780
gctcaacatg cggtcgggcg gcacgtacat cccgccggcg aggctgaggg cgctgcaggc    840
gcagatcacg gacaagagca gcaaggagta ccagcggatg gcgtgggagg cgctcaagaa    900
gagcatcaac ggcctgatca acaaggtcaa cacggccaac atcaagcaca ttgtgcccga    960
gctgtttggc gagaacctgg tgcgcggccg cggcctcttc tgccgctcca tcatgaaggc   1020
ccaggccgcc agtttgccct tcacgcccat ctacgccgcc atggccgcca ttgtcaacac   1080
caagctgccg caggtcggcg agctgctggt caagcgcctc atcatgcagt tccgcaaggg   1140
cttcaagcgc aacgacaagg ccgtctgtct gtcgtcgacc accttcctcg cccacctcat   1200
caaccagcag gtgcagcacg agatgctggc cggccagatc ctgctgctgc tgctgcacaa   1260
gccgaccgac gacagcgtcg agattgccgt gggcttctgc aaggaggttg gccagtacct   1320
cgaggagatg cagcctgcca tttccatggc cgtcttcgac cagttccgca acatcctcca   1380
cgagtccgac attgacaagc gaacgcagta catgattgag gtgctcttcc agatcaggaa   1440
ggacaagttc aaggatcacc cggccatcaa ggaggagctg gacttggtgg aggaggagga   1500
ccagatcacg cacaaggtgg agcttgatgg cgagattgat gtgcaggacg gactcaacat   1560
cttcaagtac gacccggagt gggaggagca tgaggaggca tacaagaggc tcaaggcgga   1620
gattctgggc gaagccagcg atgacgagga gggcgacgag gacgaggacg aggacgagag   1680
ctccgaagat gaagaaaacg aagagacaaa ggccatggag atcaaggacc agtctaacgc   1740
cgacttggtc aacctacgga ggaccatcta cctcaccatc atgtcgagcg ccgacccaga   1800
ggaagcagtt cacaagctga tgaagatcaa cctgcccgtc ggccaggaac ccgagctgcc   1860
ctcgatgatt gtcgagtgtt gctcgcagga gaagacgtac accaagttct ttggcttgat   1920
cggcgagcgt ttcgccaaga tcaatcggct gtggtgcgac ctctttgagc aggcctttgt   1980
caagtactac gagacgatcc accgatacga aaacaacaag ctgcggaaca ttgccatgct   2040
gtttggccac atgtttgctt ccgacgctct gggctggcac tgcctttccg tcattcacct   2100
caacgaggag gagaccacgt cgagcagccg catcttcatc aagattctgt tccagcacat   2160
ttccgaggaa atcggcctgg ctaagctccg ggcacgcatg actgacgaga cgctgcggcc   2220
cagcctcgaa ggcctcttcc ccagagagaa ccctcgcaac atccgattct ccatcaacta   2280
cttcaccagc atcggcatgg gtgtactgac cgaggagatg cgagagcacc tcatgaacat   2340
gcccaagcct gcgctgcccg cccctgctgc tcaggaccgc tcggatacgg actccgtctc   2400
gagctattcg tcttacactc actcatcata ctcttcccgc tcgcgctcac ggtcccgatc   2460
tgtgggtcgt cggagcggcg gtcgaggccg atcgctttcc cgaactccgc ctcgacgtgg   2520
cgcaaggagc cgatcctact ctgacgactc acggtcaccg tcgcggtcaa gatcacgatc   2580
ccgctccgat tccgtctcta ctcgtgggcg aaggcgagcg tcgtactcgg ccagtcctcc   2640
ccggcgtggt ggccgtcggg ttgccagcag aagccgaagc tactcgtcgg gctcctcacg   2700
gtctccgcca ccacggaacc gcggtcgcgc acgaagcaac tcgtatagtt cctacagccg   2760
ctctccatct tcttcaccac gacgcggcag agacgcagac tcggccagcc cgcctccgcg   2820
```

-continued

```
aaggggtcga ccgcgccaga gcccaccagg cggtcccgca ggtcgaagga acagctcgtc   2880

tgtcggcagc ggagggcccc gcaagaagcc ccgacgggac agccgatcgc cgtctcgcga   2940

ctattcgtcc cggtccccgt ctcggtcgcc gtcgagatct cgatcgcctc cgccggctgc   3000

gcgtggccga aggggctctt atacgccgtc acgcagccgc agcccgcctc cgcgcagggt   3060

gagggatggc tcgccgggtc gtctgagggg tgggaggtcg cctagtcctc ctttgccggt   3120

gaagaggagg cggtatgata gcgagagtgt ttctcggtcg ccgcctcctt tgaagcgcgg   3180

gagaagggat aactaaacct ttaccttttg aacgatgaat tgttcctctt gcttagattg   3240

aaacggttaa gcggagtgga attgggtggg atgggaaaac gtgtaataga ttggttgatg   3300

ggtgggaata gggaatattt acttgggtta tgcgtcacat agtagcaccc ccttttttttg   3360

cccttctttg atatcattag cgattcaata cactaattac ggacaatcac cttggcttct   3420

gtcattctat gtgcttgtga gcgaatctac tggtttgact gctgcacggt atatgtgaga   3480

tcgtggactg ctaacccctt ctttcttctt ggcaat                             3516


<210> SEQ ID NO 8
<211> LENGTH: 5714
<212> TYPE: DNA
<213> ORGANISM: Artificial Sequence
<220> FEATURE:
<223> OTHER INFORMATION: DNA fragment for transformation

<400> SEQUENCE: 8

cttaagcgac tcgaacgaca tatacccttc ccgtccatcc agatcgcgac acacacgatg     60

gcggccgtcg tcgacatgcc gcaccgcgag cgcggcaagc agcgagaagg cggcgactcg    120

taccgcccct cgaggccagc gcgttcacgc tcgcgctcgc gatcgccgcc tcgcgcgccg    180

gtgcccgtgc ggacggagga ggagaagcag gcggcggcaa aggccgagta cgagaagctg    240

ctcaacatgc ggtcgggcgg cacgtacatc ccgccggcga ggctgagggc gctgcaggcg    300

cagatcacgg acaagagcag caaggagtac cagcggatgg cgtgggaggc gctcaagaag    360

agcatcaacg gcctgatcaa caaggtcaac acggccaaca tcaagcacat tgtgcccgag    420

ctgtttggcg agaacctggt gcgcggccgc ggcctcttct gccgctccat catgaaggcc    480

caggccgcca gtttgccctt cacgcccatc tacgccgcca tggccgccat tgtcaacacc    540

aagctgccgc aggtcggcga gctgctggtc aagcgcctca tcatgcagtt ccgcaagggc    600

ttcaagcgca acgacaaggc cgtctgtctg tcgtcgacca ccttcctcgc ccacctcatc    660

aaccagcagg tgcagcacga gatgctggcc ggccagatcc tgctgctgct gctgcacaag    720

ccgaccgacg acagcgtcga gattgccgtg ggcttctgca aggaggttgg ccagtacctc    780

gaggagatgc agcctgccat ttccatggcc gtcttcgacc agttccgcaa catcctccac    840

gagtccgaca ttgacaagcg aacgcagtac atgattgagg tgctcttcca gatcaggaag    900

gacaagttca aggatcaccc ggccatcaag gaggagctgg acttggtgga ggaggaggac    960

cagatcacgc acaaggtgga gcttgatggc gagattgatg tgcaggacgg actcaacatc   1020

ttcaagtacg acccggagtg ggaggagcat gaggaggcat acaagaggct caaggcggag   1080

attctgggcg aagccagcga tgacgaggag ggcgacgagg acgaggacga ggacgagagc   1140

tccgaagatg aagaaaacga agagacaaag gccatggaga tcaaggacca gtctaacgcc   1200

gacttggtca acctacggag gaccatctac ctcaccatca tgtcgagcgc cgacccagag   1260

gaagcagttc acaagctgat gggtaccgcg gccgcctagt catcattgga taggcagatt   1320

actcagcctg aatgacatca acatgttacc catgatacaa taggtcacac aaacaagcgc   1380
```

-continued

```
taagatgcac ttggtatgac aagcccagta gtccgtttca aaagacctag atgatgaact   1440
acaacatgag gtgttgcctc ctgatccagt ccaactgcaa acgctgatgt atactcaatc   1500
aagcctgatg taaatgctgc gactcgattc gctggatatg aagatcaaag agagctctga   1560
tgggtccaat atagccgggt tttgttagga cagtccacca caccgatatt agaattggtc   1620
aagcacctta tcatttcata gagattgcgg tttctagatc tacgccagga ccgagcaagc   1680
ccagatgaga accgacgcag atttccttgg cacctgttgc ttcagctgaa tcctggcaat   1740
acgagatacc tgctttgaat attttgaata gctcgcccgc tggagagcat cctgaatgca   1800
agtaacaacc gtagaggctg acacggcagg tgttgctagg gagcgtcgtg ttctacaagg   1860
ccagacgtct tcgcggttga tatatatgta tgtttgactg caggctgctc agcgacgaca   1920
gtcaagttcg ccctcgctgc ttgtgcaata atcgcagtgg ggaagccaca ccgtgactcc   1980
catctttcag taaagctctg ttggtgttta tcagcaatac acgtaattta aactcgttag   2040
catggggctg atagcttaat taccgtttac cagtgccgcg gttctgcagc tttccttggc   2100
ccgtaaaatt cggcgaagcc agccaatcac cagctaggca ccagctaaac cctataatta   2160
gtctcttatc aacaccatcc gctcccccgg gatcaatgag gagaatgagg gggatgcggg   2220
gctaaagaag cctacataac cctcatgcca actcccagtt tacactcgtc gagccaacat   2280
cctgactata agctaacaca gaatgcctca atcctgggaa gaactggccg ctgataagcg   2340
cgcccgcctc gcaaaaacca tccctgatga atggaaagtc cagacgctgc ctgcggaaga   2400
cagcgttatt gatttcccaa agaaatcggg catcctttca gaggccgaac tgaagatcac   2460
agaggcctcc gctgcagatc ttgtgtccaa gctggcggcc ggagagttga cctcggtgga   2520
agttacgcta gcattctgta aacgggcagc aatcgcccag cagttagtag ggtcccctct   2580
acctctcagg gagatgtaac aacgccacct tatgggacta tcaagctgac gctggcttct   2640
gtgcagacaa actgcgccca cgagttcttc cctgacgccg ctctcgcgca ggcaagggaa   2700
ctcgatgaat actacgcaaa gcacaagaga cccgttggtc cactccatgg cctccccatc   2760
tctctcaaag accagcttcg agtcaaggta caccgttgcc cctaagtcgt tagatgtccc   2820
tttttgtcag ctaacatatg ccaccagggc tacgaaacat caatgggcta catctcatgg   2880
ctaaacaagt acgacgaagg ggactcggtt ctgacaacca tgctccgcaa agccggtgcc   2940
gtcttctacg tcaagacctc tgtcccgcag accctgatgg tctgcgagac agtcaacaac   3000
atcatcgggc gcaccgtcaa cccacgcaac aagaactggt cgtgcggcgg cagttctggt   3060
ggtgagggtg cgatcgttgg gattcgtggt ggcgtcatcg gtgtaggaac ggatatcggt   3120
ggctcgattc gagtgccggc cgcgttcaac ttcctgtacg gtctaaggcc gagtcatggg   3180
cggctgccgt atgcaaagat ggcgaacagc atggagggtc aggagacggt gcacagcgtt   3240
gtcgggccga ttacgcactc tgttgagggt gagtccttcg cctcttcctt cttttcctgc   3300
tctataccag gcctccactg tcctcctttc ttgcttttta tactatatac gagaccggca   3360
gtcactgatg aagtatgtta gacctccgcc tcttcaccaa atccgtcctc ggtcaggagc   3420
catggaaata cgactccaag gtcatcccca tgccctggcg ccagtccgag tcggacatta   3480
ttgcctccaa gatcaagaac ggcgggctca atatcggcta ctacaacttc gacggcaatg   3540
tccttccaca ccctcctatc ctgcgcggcg tggaaaccac cgtcgccgca ctcgccaaag   3600
ccggtcacac cgtgaccccg tggacgccat acaagcacga tttcggccac gatctcatct   3660
cccatatcta cgcggctgac ggcagcgccg acgtaatgcg cgatatcagt gcatccggcg   3720
```

-continued

```
agccggcgat tccaaatatc aaagacctac tgaacccgaa catcaaagct gttaacatga   3780

acgagctctg ggacacgcat ctccagaagt ggaattacca gatggagtac cttgagaaat   3840

ggcgggaggc tgaagaaaag gccgggaagg aactggacgc catcatcgcg ccgattacgc   3900

ctaccgctgc ggtacggcat gaccagttcc ggtactatgg gtatgcctct gtgatcaacc   3960

tgctggattt cacgagcgtg gttgttccgg ttacctttgc ggataagaac atcgataaga   4020

agaatgagag tttcaaggcg gttagtgagc ttgatgccct cgtgcaggaa gagtatgatc   4080

cggaggcgta ccatggggca ccggttgcag tgcaggttat cggacggaga ctcagtgaag   4140

agaggacgtt ggcgattgca gaggaagtgg ggaagttgct gggaaatgtg gtgactccat   4200

agctaataag tgtcagatag caatttgcac aagaaatcaa taccagcaac tgtaaataag   4260

cgctgaagtg accatgccat gctacgaaag agcagaaaaa aacctgccgt agaaccgaag   4320

agatatgaca cgcttccatc tctcaaagga agaatccctt cagggttgcg tttccagtct   4380

agacgcgttg tcaagtacta cgagacgatc caccgatacg aaaacaacaa gctgcggaac   4440

attgccatgc tgtttggcca catgtttgct tccgacgctc tgggctggca ctgcctttcc   4500

gtcattcacc tcaacgagga ggagaccacg tcgagcagcc gcatcttcat caagattctg   4560

ttccagcaca tttccgagga aatcggcctg gctaagctcc gggcacgcat gactgacgag   4620

acgctgcggc ccagcctcga aggcctcttc cccagagaga accctcgcaa catccgattc   4680

tccatcaact acttcaccag catcggcatg ggtgtactga ccgaggagat gcgagagcac   4740

ctcatgaaca tgcccaagcc tgcgctgccc gcccctgctg ctcaggaccg ctcggatacg   4800

gactccgtct cgagctattc gtcttacact cactcatcat actcttcccg ctcgcgctca   4860

cggtcccgat ctgtgggtcg tcggagcggc ggtcgaggcc gatcgctttc ccgaactccg   4920

cctcgacgtg gcgcaaggag ccgatcctac tctgacgact cacggtcacc gtcgcggtca   4980

agatcacgat cccgctccga ttccgtctct actcgtgggc gaaggcgagc gtcgtactcg   5040

gccagtcctc cccggcgtgg tggccgtcgg gttgccagca gaagccgaag ctactcgtcg   5100

ggctcctcac ggtctccgcc accacggaac cgcggtcgcg cacgaagcaa ctcgtatagt   5160

tcctacagcc gctctccatc ttcttcacca cgacgcggca gagacgcaga ctcggccagc   5220

ccgcctccgc gaaggggtcg accgcgccag agcccaccag gcggtcccgc aggtcgaagg   5280

aacagctcgt ctgtcggcag cggagggccc cgcaagaagc cccgacggga cagccgatcg   5340

ccgtctcgcg actattcgtc ccggtccccg tctcggtcgc cgtcgagatc tcgatcgcct   5400

ccgccggctg cgcgtggccg aaggggctct tatacgccgt cacgcagccg cagcccgcct   5460

ccgcgcaggg tgagggatgg ctcgccgggt cgtctgaggg gtgggaggtc gcctagtcct   5520

cctttgccgg tgaagaggag gcggtatgat agcgagagtg tttctcggtc gccgcctcct   5580

ttgaagcgcg ggagaaggga taactaaacc tttacctttt gaacgatgaa ttgttcctct   5640

tgcttagatt gaaacggtta agcggagtgg aattgggtgg gatgggaaaa cgtgtaatag   5700

attggttgac tagt                                                     5714
```

<210> SEQ ID NO 9
<211> LENGTH: 37
<212> TYPE: DNA
<213> ORGANISM: Artificial Sequence
<220> FEATURE:
<223> OTHER INFORMATION: Oligo DNA for PCR

<400> SEQUENCE: 9

```
atgcatctta agcgactcga acgacatata cccttcc                            37
```

-continued

```
<210> SEQ ID NO 10
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 10

atggtaccca tcagcttgtg aactgcttcc tct                                 33


<210> SEQ ID NO 11
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 11

atacgcgttg tcaagtacta cgagacgatc cac                                 33


<210> SEQ ID NO 12
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 12

atactagtca accaatctat tacacgtttt ccc                                 33
```

TRICHODERMA REESEI MUTANT AND PROTEIN PRODUCTION METHOD

TECHNICAL FIELD

This disclosure relates to a *Trichoderma reesei* mutant strain having an enhanced protein-producing ability, and a protein production method using the mutant strain.

BACKGROUND

*Trichoderma reesei* is known to have a high protein-producing ability, and studies have heretofore been made on protein production using this filamentous fungus. *Trichoderma reesei* has an excellent ability of producing, among proteins, particularly a cellulase classified as a saccharifying enzyme, and to further enhance, for example, the cellulase production amount, overexpression or deletion of the factor controlling the cellulase production is performed. In Juliano de Oliveira Porciuncula et al., "Single Nucleotide Polymorphism Analysis of a *Trichoderma reesei* Hyper-Cellulolytic Mutant Developed in Japan," Bioscience, Biotechnology, and Biochemistry, Volume 77, 2013, Issue 3, pp 534-543, a *Trichoderma reesei* mutant strain having a high cellulase-producing ability is acquired by reducing, among factors controlling the cellulase production in *Trichoderma reesei*, the function of Cre1 which is a transcription factor repressing the cellulase production.

As described above, a transcription factor that is one of factors controlling protein production in *Trichoderma reesei* is identified, but this is considered to be merely a part of the control mechanism. There is thus a need to acquire a *Trichoderma reesei* mutant strain having enhanced protein-producing ability by searching for a novel factor controlling the protein production in *Trichoderma reesei* and provide a protein production method using the *Trichoderma reesei* mutant strain.

SUMMARY

We found that when a previously unknown control factor for the protein production in *Trichoderma reesei* is identified, the protein production amount in *Trichoderma reesei* can be increased, and we found that the protein production property can be improved by cultivating a *Trichoderma reesei* mutant strain reduced in the function of a polypeptide consisting of the amino acid sequence represented by SEQ ID NO: 2.

We thus provide (1) to (5):

(1) A *Trichoderma reesei* mutant strain in which a function of a polypeptide consisting of the amino acid sequence represented by SEQ ID NO: 2 is reduced.

(2) The *Trichoderma reesei* mutant strain according to (1), in which two amino acid residues of 347th and 348th in the amino acid sequence represented by SEQ ID NO: 2 are deleted.

(3) A method of producing a protein, the method including a step of cultivating the *Trichoderma reesei* mutant strain according to (1) or (2).

(4) A method of producing a cellulase, the method including a step of cultivating the *Trichoderma reesei* mutant strain according to (1) or (2).

(5) A method of producing a sugar from a cellulose-containing biomass, the method including:

step a of producing a cellulase by cultivating a *Trichoderma reesei* mutant strain in which a function of a polypeptide consisting of the amino acid sequence represented by SEQ ID NO: 2 is reduced; and step b of saccharifying the biomass by using the cellulase obtained in the step a.

The *Trichoderma reesei* reduced in the function of a polypeptide consisting of the amino acid sequence represented by SEQ ID NO: 2 has an improved protein-producing ability, compared to *Trichoderma reesei* in which the function of the polypeptide is not reduced. In addition, use of the *Trichoderma reesei* enables enhanced production of a protein. Furthermore, when the produced protein is a cellulase, there is also obtained an unexpected effect that various specific activities of the cellulase are improved.

DETAILED DESCRIPTION

Mutation is introduced into a parent strain of *Trichoderma reesei* of a microorganism originally having an excellent protein-producing ability and the protein-producing ability is thereby further increased. Accordingly, the *Trichoderma reesei* parent strain is not limited to a wild strain, and a *Trichoderma reesei* mutant strain resulting from modification to increase the protein-producing ability can also be favorably used as the parent strain. For example, for the *Trichoderma reesei* mutant strain, a mutant strain subjected to a mutation treatment with a mutagen or UV irradiation and the like to improve the protein productivity can be utilized as the above-described parent strain. Specific examples of the mutant strain used as the parent strain include known mutant strains derived from *Trichoderma reesei* such as QM6a strain (NBRC31326), QM9414 strain (NBRC31329), PC-3-7 strain (ATCC66589), QM9123 strain (NBRC31327), RutC-30 strain (ATCC56765), CL-847 strain (Enzyme. Microbiol. Technol. 10, 341-346 (1988)), MCG77 strain (Biotechnol. Bioeng. Symp. 8, 89 (1978)), MCG80 strain (Biotechnol. Bioeng. 12, 451-459 (1982)), and derivative strains thereof. QM6a strain, QM9414 strain, and QM9123 strain are available from NBRC (NITE Biological Resource Center), and PC-3-7 strain and RutC-30 strain are available from ATCC (American Type Culture Collection).

The polypeptide consisting of the amino acid sequence represented by SEQ ID NO: 2 is a polypeptide that *Trichoderma reesei* has, and in the National Center for Biotechnology Information, this is also registered as a predicted protein (EGR50654) that *Trichoderma reesei* QM6a strain has. The polypeptide consisting of the amino acid sequence represented by SEQ ID NO: 2 is a polypeptide whose function is not known, but Censerved Domain Architecture Retrieval Tool of National Center for Biotechnology Information discloses that 95th to 277th amino acid residues on the N-terminal side have "Middle domain of eukaryotic initiation factor 4G domain" (in the present description, sometimes referred to as MIF4G domain) and 380th to 485th amino acid residues on the N-terminal side have MA-3 domain. Two domains of MIF4G and MA-3 are known to have a function of binding to DNA or RNA (Biochem. 44, 12265-12272 (2005), Mol. Cell. Biol. 1, 147-156 (2007)). From these descriptions, the polypeptide consisting of the amino acid sequence represented by SEQ ID NO: 2 is estimated to have at least a function of binding to DNA and/or RNA.

Reduction of the function of the polypeptide consisting of the amino acid sequence represented by SEQ ID NO: 2 indicates the state where the base sequence encoding the amino acid sequence represented by SEQ ID NO: 2 undergoes mutation and thus the function of the polypeptide is reduced or the function is deleted. In addition, when a base sequence other than the base sequence encoding the amino acid sequence represented by SEQ ID NO: 2 undergoes mutation and thus the polypeptide consisting of the amino acid sequence represented by SEQ ID NO: 2 is reduced in the expression level or loses expression, this is also encompassed by the reduction of the function of the polypeptide consisting of the amino acid sequence represented by SEQ ID NO: 2. The mutation of the base sequence is caused by substitution, deletion, insertion, duplication and the like.

Specific example of the gene encoding the polypeptide consisting of the amino acid sequence represented by SEQ ID NO: 2 include the base sequence represented by SEQ ID NO: 1.

The specific methods of reducing the function of the polypeptide consisting of the amino acid sequence represented by SEQ ID NO: 2 include a method of introducing such mutation as to cause a total deletion of MIF4G domain and/or MA-3 domain, a partial deletion of MIF4G domain and/or MA-3 domain, a change in the configuration relationship between MIF4G domain and MA-3 domain, or a total deletion of the polypeptide consisting of the amino acid sequence represented by SEQ ID NO: 2.

Deletion of MIF4G domain and/or MA-3 domain denotes loss of the whole or a part of the domain, change of the whole or a part of the domain into different amino acid(s), or a combination thereof. More specifically, the term means that in the amino acid sequence represented by SEQ ID NO: 2, the sequence identity to the amino acid sequence of MIF4G domain or MA-3 domain decreases to 80% or less, preferably to 50% or less, more preferably to 20% or less, more preferably to 10% or less, more preferably to 5% or less, more preferably to 3% or less, more preferably to 1% or less, and most preferably to 0%.

The change in the configuration relationship between MIF4G domain and MA-3 domain is caused by mutation where amino acid deletion, substitution or addition occurs in the amino acid sequence positioned between MIF4G domain and MA-3 domain. The MIF4G domain and MA-3 domain are called a protein domain, and the protein domain constitutes a part of the protein sequence structure and is a presence having a function. In having a plurality of domains, a conformation consisting of a plurality of domains constitutes a part of the protein conformation and therefore, when the configuration between domains is changed, this leads to a change in the protein conformation and reduction in the protein function. For example, streptokinase produced by genus *Streptococcus* has a total of three kinds of domains, i.e., α domain, β domain and γ domain, and α domain and β domain are interconnected by 12 amino acid residues, and β domain and γ domain are interconnected by 15 amino acid residues. In Biochem. Biophys. Acta. 9, 1730-1737 (2010), it is stated that the streptokinase activity is reduced or lost due to occurrence of mutation such as substitution, addition or deletion of amino acid residues in the amino acid sequences positioned between α domain and β domain and between β domain and γ domain. The substitution in the amino acid sequence between domains are described in Tables 1 and 2, and the deletion or addition in the amino acid sequence between domains are described in Tables 5 and 6.

In this way, it is known that even when an amino acid mutation such as deletion, substitution or addition does not occur in the amino acid sequence itself constituting the domain, the protein function is reduced due to occurrence of an amino acid mutation such as deletion, substitution or addition in the amino acid sequence positioned between two domains. Herein, the amino sequence positioned between MIF4G domain and MA-3 domain indicates the region from 278th to 379th amino acid residues on the N-terminal side in the amino acid sequence of SEQ ID NO: 2. Furthermore, herein, the base sequence encoding the amino sequence positioned between MIF4G domain and MA-3 domain indicates the region of 832nd to 1137th base sequences in the base sequence represented by SEQ ID NO: 1.

Specific examples of the reduction in the function of a polypeptide consisting of the amino acid sequence represented by SEQ ID NO: 2, which is caused by occurrence of mutation such as deletion, substitution or addition in the amino acid sequence positioned between MIF4G domain and MA-3 domain, include a mutation where any of 1039th to 1044th bases in the base sequence represented by SEQ ID NO: 1 is deleted. This base deletion is a deletion of two, 347th and 348th, amino acid residues in the amino acid sequence positioned between MIF4G domain and MA-3 domain of a polypeptide consisting of the amino acid sequence represented by SEQ ID NO: 2. we believe that due to the mutation above, the amino acid sequence interconnecting MIF4G domain and MA-3 domain is shortened and thus the three-dimensional configuration relationship between MIF4G domain and MA-3 domain is changed.

Accordingly, a preferred example of the *Trichoderma reesei* reduced in the function of a polypeptide consisting of the amino acid sequence represented by SEQ ID NO: 2 includes a *Trichoderma reesei* mutant strain in which two, 347th and 348th, amino acid residues in the amino acid sequence represented by SEQ ID NO: 2 are deleted. The phrase "two, 347th and 348th, amino acid residues are deleted" means that at least those two amino acid residues are deleted in the amino acid sequence represented by SEQ ID NO: 2, and preferred examples are where two, 347th and 348th, amino acids are deleted, and an example where in addition to the deletion of those two amino acids, MIF4G domain and/or MA-3 domain are entirely deleted or MIF4G domain and/or MA-3 domain are partially deleted.

Deletion of two, 347th and 348th, amino acid residues in the amino acid sequence represented by SEQ ID NO: 2, the total deletion of MIF4G domain and/or MA-3 domain, partial deletion of MIF4G domain and/or MA-3 domain, and total deletion of a polypeptide consisting of the amino acid sequence represented by SEQ ID NO: 2 are caused by a frame shift or stop codon mutation by base deletion, insertion, substitution and the like within the gene sequence encoding a polypeptide consisting of the amino acid sequence represented by SEQ ID NO: 2.

With respect to the polypeptide consisting of the amino acid sequence represented by SEQ ID NO: 2, the reduction of expression level or the loss of expression is caused by mutation in the promoter or terminator region of the gene encoding the amino acid sequence represented by SEQ ID NO: 2. In general, the promoter and terminator regions correspond to a region of hundreds of bases in length before and after the gene participating in transcription, and specific examples of the base sequence containing a promoter and terminator participating in transcription of the polypeptide consisting of the amino acid sequence represented by SEQ ID NO: 2 include the base sequence represented by SEQ ID NO: 7.

At the introduction of genetic mutation, existing genetic mutation methods such as a mutation treatment with a mutagen or UV irradiation known to one skilled in the art, gene recombination such as homologous recombination using a selection marker, or mutation by a transposon can be used.

Our *Trichoderma reesei* mutant strain has an enhanced protein-producing ability, compared with *Trichoderma reesei* in which the function of the polypeptide consisting of the amino acid sequence represented by SEQ ID No: 2 is not reduced. When our *Trichoderma reesei* mutant strain is cultivated, the protein concentration increases, compared to a culture solution of *Trichoderma reesei* in which the function of the polypeptide consisting of the amino acid sequence represented by SEQ ID No: 2 is not reduced. Furthermore, when the protein is an enzyme, the enzyme specific activity increases. The protein concentration increase rate or the enzyme specific activity increase rate is not particularly limited as long as the concentration or specific activity is increased, but the increase rate is preferably 20% or more.

We also provide a protein production method including a step of cultivating *Trichoderma reesei* reduced in the function of the polypeptide consisting of the amino acid sequence represented by SEQ ID NO: 2.

The culture medium composition in the cultivating step is not particularly limited as long as it is a culture medium composition where *Trichoderma reesei* can produce a protein, and a known culture medium composition for a filamentous fungus belonging to genus *Trichoderma* can be employed. As the nitrogen source, for example, polypeptone, bouillon, CSL, or soybean cake can be used. In addition, an inducer for producing a protein may be added to the culture medium.

The culture method is not particularly limited, and the culture can be performed, for example, by liquid culture using a centrifuge tube, a flask, a jar fermenter, a tank or the like, or solid culture using a plate or the like. *Trichoderma reesei* is preferably cultivated in aerobic conditions, and among these culture methods, submerged culture of performing the culture by using a jar fermenter or while aerating and stirring in a tank is preferred. The aeration rate is preferably approximately from 0.1 vvm to 2.0 vvm, more preferably from 0.3 vvm to 1.5 vvm, still more preferably from 0.5 vvm to 1.0 vvm. The culture temperature is preferably approximately from 25° C. to 35° C., more preferably from 25° C. to 31° C. The pH condition during culture is preferably pH 3.0 to 7.0, more preferably pH 4.0 to 6.0. As for the culture period, the culture is performed under conditions allowing for protein production until a recoverable amount of proteins are accumulated. Usually, the culture period is approximately from 24 hours to 240 hours, more preferably from 36 hours to 192 hours.

The protein produced herein is not particularly limited, but a protein secreted outside the fungus body can be efficiently produced. Among them, the protein is preferably an enzyme, more preferably a saccharifying enzyme such as cellulase, amylase, invertase, chitinase, or pectinase, still more preferably a cellulase.

The cellulase produced herein contains various hydrolases and contains an enzyme having a decomposition activity for xylan, cellulose and hemicellulose. Specific examples thereof include cellobiohydrolase (EC 3.2.1.91) that produces cellobiose by hydrolysis of a cellulose chain, endoglucanase (EC 3.2.1.4) that hydrolyzes a cellulose chain from its central portion, β-glucosidase (EC 3.2.1.21) that hydrolyzes cellooligosaccharides or cellobiose, xylanase (EC 3.2.1.8) that acts on hemicellulose or particularly on xylan, and β-xylosidase (EC 3.2.1.37) that hydrolyzes xylooligosaccharides. As described above, the confirmation of enhancement of cellulase specific activity for confirming the enhancement of the protein-producing ability of the *Trichoderma reesei* mutant strain is performed by determining that any of specific activities of these hydrolases is enhanced.

The β-glucosidase specific activity is measured by the following method. First, 10 μL of an enzyme dilution is added to 90 μL of 50 mM acetate buffer containing 1 mM p-nitrophenyl-β-glucopyranoside (produced by Sigma-Aldrich Japan), and the mixture is allowed to react at 30° C. for 10 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity, and the specific activity is calculated by dividing it by the protein amount.

The β-xylosidase specific activity is measured by the following method. First, 10 μL of an enzyme dilution is added to 90 μL of 50 mM acetate buffer containing 1 mM p-nitrophenyl-β-xylopyranoside (produced by Sigma-Aldrich Japan), and the mixture is allowed to react at 30° C. for 30 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity, and the specific activity is calculated by dividing it by the protein amount.

The cellobiohydrolase specific activity is measured by the following method. First, 10 μL of an enzyme dilution is added to 90 μL of 50 mM acetate buffer containing 1 mM p-nitrophenyl-β-lactopyranoside (produced by Sigma-Aldrich Japan), and the mixture is allowed to react at 30° C. for 60 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity, and the specific activity is calculated by dividing it by the protein amount.

In producing our cellulase, cellulose and/or xylan may be added as an inducer to the culture medium. A biomass containing cellulose or xylan may be added as an inducer. Specific examples of the biomass containing cellulose or xylan include not only plants such as seed plant, pteridophyte, bryophyte, algae, and water plant, but also waste building materials. The seed plants are classified into gymnosperms and angiosperms, and both can be used favorably. The angiosperms are further classified into monocotyledons and dicotyledons. Specific examples of the monocotyledons include bagasse, switchgrass, napier grass, Erianthus, corn stover, corncob, rice straw, and wheat straw, and specific examples of the dicotyledons used preferably include beet pulp, *eucalyptus*, oak, and white birch.

As the inducer containing cellulose and/or xylan, a pretreated product may be used. The pretreatment method is not particularly limited, but, for example, known methods such as acid treatment, sulfuric acid treatment, dilute sulfuric acid treatment, alkali treatment, hydrothermal treatment, subcritical treatment, fine grinding treatment, and steaming treatment can be used. As the pretreated biomass containing cellulose and/or xylan, pulp may be used.

The method of recovering protein contained in the culture solution where the *Trichoderma reesei* mutant is cultivated is not particularly limited, but the protein can be recovered by removing the *Trichoderma reesei* fungus body from the culture solution. Examples of the method of removing the fungus body include centrifugation, membrane separation, filter press and the like.

Furthermore, when the culture solution in which the *Trichoderma reesei* mutant is cultivated is used as a proteindissolving liquid without removing the fungus body therefrom, the culture solution is preferably treated so that the fungus body cannot grow therein. The treatment method for preventing the fungus body from growing includes heat treatment, chemical treatment, acid/alkali treatment, UV treatment and the like.

When the protein is an enzyme, the culture solution in which the fungus body is removed or prevented from growing can be used directly as an enzyme solution.

Furthermore, when the protein is a cellulase, sugar can be produced by saccharifying a cellulose-containing biomass with use of the cellulase.

As the cellulose-containing biomass, the same biomass as the cellulose-containing biomass described above as an inducer, or a pretreated biomass can be used.

The cellulase obtained by cultivating our *Trichoderma reesei* mutant strain is a cellulase obtained by cultivating the *Trichoderma reesei* mutant strain reduced in the function of the polypeptide consisting of the amino acid sequence represented by SEQ ID NO: 2, and since the specific activity of, particularly, β-glucosidase and the like is high compared to the cellulase obtained by cultivating *Trichoderma reesei* in which the function of the polypeptide is not reduced, a saccharified solution having a high glucose concentration can be obtained by efficiently de-composing the cellulose-containing biomass, and thus a larger quantity of sugar can be obtained.

The saccharification reaction conditions are not particularly limited, but the saccharification reaction temperature is preferably 25 to 60° C., more preferably 30 to 55° C. The saccharification reaction time is preferably 2 to 200 hours. The pH of the saccharification reaction is preferably pH 3.0 to 7.0, more preferably pH 4.0 to 6.0. In a genus *Trichoderma*-derived cellulase, the most preferred pH for the reaction is 5.0. Furthermore, since the pH changes in the process of hydrolysis, the reaction is preferably conducted while adding a buffer solution to the reaction solution or keeping the pH constant by using an acid or an alkali.

In separating and recovering an enzyme from the saccharified solution, the enzyme can be recovered on the non-permeation side by filtrating the saccharified solution through an ultrafiltration membrane or the like, and if desired, as a pre-step to filtration, solid matter may be removed from the saccharified solution. The recovered enzyme can again be used for the saccharification reaction.

EXAMPLES

Our mutants and methods are described specifically below by referring to Examples.

Reference Example 1: Method of Measuring Protein Concentration

A reagent for measuring protein concentration (Quick Start Bradford protein assay, produced by Bio-Rad) was used. 5 μL of a diluted filamentous fungus culture solution was added to 250 μL of the protein concentration measurement reagent returned to room temperature and after leaving the mixture to stand at room temperature for 5 minutes, the absorbance at 595 nm was measured using a microplate reader. Using BSA as a standard, the protein concentration was calculated based on the calibration curve.

Reference Example 2: Method of Measuring Specific Activity of Cellulase Method of Measuring β-Glucosidase Specific Activity 10 μL of an enzyme dilution was added to 90 μL of 50 mM acetate buffer containing 1 mM p-nitrophenyl-β-glucopyranoside (produced by Sigma-Aldrich Japan), and the mixture was allowed to react at 30° C. for 10 minutes. Then, 10 μL of 2 M sodium carbonate was added and mixed well to stop the reaction, and the increase in absorbance at 405 nm was measured. Release of 1 μmol of p-nitrophenol per minute was defined as 1 U of activity, and the specific activity was calculated by dividing it by the protein amount.

Method of Measuring β-Xylosidase Specific Activity

10 μL of an enzyme dilution was added to 90 μL of 50 mM acetate buffer containing 1 mM p-nitrophenyl-β-xylopyranoside (produced by Sigma-Aldrich Japan), and the mixture was allowed to react at 30° C. for 30 minutes. Then, 10 μL of 2 M sodium carbonate was added and mixed well to stop the reaction, and the increase in absorbance at 405 nm was measured. Release of 1 μmol of p-nitrophenol per minute was defined as 1 U of activity, and the specific activity was calculated by dividing it by the protein amount.

Method of Measuring Cellobiohydrolase Specific Activity

10 μL of an enzyme dilution was added to 90 μL of 50 mM acetate buffer containing 1 mM p-nitrophenyl-β-lactopyranoside (produced by Sigma-Aldrich Japan), and the mixture was allowed to react at 30° C. for 60 minutes. Then, 10 μL of 2 M sodium carbonate was added and mixed well to stop the reaction, and the increase in absorbance at 405 nm was measured. Release of 1 μmol of p-nitrophenol per minute was defined as 1 U of activity, and the specific activity was calculated by dividing it by the protein amount.

Reference Example 3: Saccharification Test of Cellulose-Containing Biomass

As the cellulose-containing biomass, Arbocel (registered trademark) B800 (produced by J. Rettenmaier & Sohne) or a bagasse powdered to an average particle diameter of 100 μm was used. As the enzyme solution, a filtrate obtained by sampling 1 ml of a culture solution of *Trichoderma reesei* or *Trichoderma reesei* mutant strain, centrifuging the sampled culture solution, recovering a supernatant after removal of fungus body, and filtrating the supernatant through a 0.22 μm filter, was used.

Saccharification Reaction

100 μL of 1 M sodium acetate buffer as buffer for saccharification reaction, 2 μL of a 50 g/L erythromycin solution for prevention of proliferation of miscellaneous bacteria, and 0.1 g of, as the target for saccharification, Arbocel (registered trademark) B800 (produced by J. Rettenmaier & Sohne) or a bagasse powdered to an average particle diameter of 100 μm were added, and after adding 450 μL of enzyme solution when using Arbocel (registered trademark) B800 as the cellulose-containing biomass or adding 400 μL of enzyme solution when using bagasse as the cellulose-containing biomass, the mixture was diluted with sterile water to make a total of 1 mL and then put in a 2 mL tube. A saccharification reaction was performed under the temperature condition of 50° C. for 30 hours, a supernatant after centrifugation of the saccharified product was recovered as a saccharified solution, and a 1 N NaOH solution in an amount of 1/10 of the recovered saccharified solution was added to stop the enzyme reaction. The glucose concentration in the saccharified solution after stopping the reaction was measured by UPLC described below.

Measurement of Glucose Concentration

Glucose was quantitatively analyzed under the following conditions by using ACQUITY UPLC system (Waters). The quantitative analysis was performed based on a calibration curve prepared from a standard sample of glucose.

Column: AQUITY UPLC BEH Amide 1.7 μm 2.1×100 mm Column

Separation Method: HILIC

Mobile phase: mobile phase A: 80% acetonitrile, aqueous 0.2% TEA solution, and mobile phase B: 30% acetonitrile, an aqueous 0.2% TEA solution, in accordance with the following gradient. The gradient was a linear gradient reaching the mixing ratio corresponding to the time below.

Initiation condition: (A 99.90%, B 0.10%), 2 minutes after initiation: (A 96.70%, B 3.30%), 3.5 minutes after initiation: (A 95.00%, B 5.00%), 3.55 minutes after initiation: (A 99.90%, B 0.10%), 6 minutes after initiation: (A 99.90%, B 0.10%)

Detection method: ELSD (evaporative light scattering detector)

Flow rate: 0.3 mL/min

Temperature: 55° C.

Example 1

Preparation of *Trichoderma reesei* QM9414 Mutant Strain I Reduced in the Function of Polypeptide Consisting of the Amino Acid Sequence Represented by SEQ ID NO: 2

The *Trichoderma reesei* mutant strain reduced in the function of the polypeptide consisting of the amino acid sequence represented by SEQ ID NO: 2 was produced by preparing a DNA fragment consisting of the gene sequence represented by SEQ ID NO: 3 as a DNA fragment containing a gene encoding the polypeptide consisting of the amino acid sequence represented by SEQ ID NO: 2, in which the function of the polypeptide consisting of the amino acid sequence represented by SEQ ID NO: 2 is reduced, and transforming the DNA fragment into *Trichoderma reesei* QM9414 strain. By this method, a *Trichoderma reesei* mutant strain in which from 1039th to 1044th bases are deleted in SEQ ID NO: 1 to have a polypeptide consisting of an amino acid sequence in which two, 347th and 348th, amino acid residues are deleted in SEQ ID NO: 2, is obtained. Acetamide and acetamidase (AmdS) gene (amdS) capable of decomposing acetamide were used as selection markers for introducing the DNA fragment. To allow the DNA fragment consisting of the base sequence represented by SEQ ID NO: 3 to be introduced upstream and downstream of the amdS-containing DNA sequence, a plasmid for mutation introduction was prepared to add a portion homologous to the gene sequence of the *Trichoderma reesei* QM9414 strain.

Specifically, a DNA fragment obtained by treating a synthesized DNA fragment shown by SEQ ID NO: 4 with restriction enzymes AflII and KpnI was used as the upstream DNA fragment. In addition, PCR was conducted using genomic DNA extracted in a usual manner from the *Trichoderma reesei* QM9414 strain and oligo DNAs represented by SEQ ID NOs: 5 and 6, and a DNA fragment obtained by treating the resulting amplified fragment with restriction enzymes MluI and SpeI was used as the downstream DNA fragment. The upstream and downstream DNA fragments were introduced into an amdS-inserted plasmid by using restriction enzymes AflII and KpnI and restriction enzymes MluI and SpeI, respectively, to construct a plasmid for mutation introduction. The plasmid for mutation introduction was then treated with restriction enzymes PacI and SphI, and the *Trichoderma reesei* QM9414 strain (NBRC #31329) was transformed with the obtained DNA fragment shown by SEQ ID NO: 3. The manipulations involving the molecular biological technique were performed as described in Molecular cloning, laboratory manual, 1st, 2nd, 3rd (1989). In addition, the transformation was carried out using a standard technique, i.e., a protoplast PEG method, and specifically, was performed as described in Gene, 61, 165-176 (1987). The obtained *Trichoderma reesei* mutant strain was used as QM9414 mutant strain I in the following experiments.

Example 2

Protein Production Test Using QM9414 Mutant Strain I (Flask Cultivation)

After spores of QM9414 mutant strain I produced in Example 1 were diluted with physiological saline to be $1.0\times10^7$/mL, 0.1 mL of the diluted spore solution was inoculated into 10 mL of a flask medium shown in Table 1, which is placed in a 50 mL baffled flask, and the flask medium was incubated in a shaker under the conditions of 28° C. and 120 rpm for 120 hours.

TABLE 1

| | |
|---|---|
| Arbocel B800 (produced by J. Rettenmaier & Sohne) | 20 g |
| 5× Mandel's solution* | 200 mL |
| 10× Ammonium tartrate solution** | 100 mL |
| Corn steep liquor | 50 g |
| Trace element solution*** | 1 mL |
| Tween 80 | 0.5 mL |
| PE-M | 1 mL |
| | (per 1 L) |

*The 5×Mandel's solution contains 7 g/L $(NH_4)_2SO_4$, 10 g/L $KH_2PO_4$, 2 g/L $CaCl_2$•$2H_2O$, and 1.5 g/L $MgSO_4$•$7H_2O$.

**The 10× Ammonium tartrate solution contains 92 g/L ammonium tartrate.

***The trace element solution contains 0.3 g/L $H_3BO_3$, 1.3 g/L $(NH_4)_6Mo_7O_{24}$•$4H_2O$, 5 g/L $FeCl_3$•$6H_2O$, 2 g/L $CuSO_4$•$5H_2O$, 0.4 g/L $MnCl_2$•$4H_2O$, and 10 g/L $ZnCl_2$.

Collection of Culture Solution

After 120 Hours from the start of cultivation, 1 mL of the culture solution was collected. The culture solution was centrifuged under the conditions of 15,000×g and 4° C. for 10 minutes to obtain a supernatant. The supernatant was filtrated through a 0.22 μm filter, and the filtrate was used as a cellulase solution in the following experiments.

Measurements of Protein Concentration and Various Specific Activities of Cellulase The protein concentration in the culture solution at 120 hours from the start of cultivation was measured using the technique described in Reference Example 1 and, subsequently, the specific activities of the cellulase were measured by the method described in Reference Example 2. The results are shown in Table 2.

Example 3

Production of *Trichoderma reesei* QM9414 Mutant Strain II Reduced in the Function of Polypeptide Consisting of the Amino Acid Sequence Represented by SEQ ID NO: 2

The *Trichoderma reesei* mutant strain reduced in the function of the polypeptide consisting of the amino acid sequence represented by SEQ ID NO: 2 was produced by preparing a DNA fragment consisting of the gene sequence represented by SEQ ID NO: 8, and transforming the DNA fragment into *Trichoderma reesei* QM9414 strain. By this method, amdS is inserted between 1206th and 1207th bases in SEQ ID NO: 1, and a *Trichoderma reesei* mutant strain reduced in the function of SEQ ID NO: 2 is obtained. For allowing the DNA fragment consisting of the base sequence represented by SEQ ID NO: 8 to be introduced upstream and downstream of the amdS-containing DNA sequence, a plasmid for mutation introduction was prepared to add a portion homologous to the gene sequence of the *Trichoderma reesei* QM9414 strain.

Specifically, PCR was conducted using genomic DNA extracted in a usual manner from the *Trichoderma reesei* QM9414 strain and oligo DNAs represented by SEQ ID NOs: 9 and 10, and a DNA fragment obtained by treating the resulting amplified fragment with restriction enzymes AflII and KpnI was used as the upstream fragment. In addition, PCR was conducted using genomic DNA and oligo DNAs represented by SEQ ID NOs: 11 and 12, and a DNA fragment obtained by treating the resulting amplified fragment with restriction enzymes MluI and SpeI was used as the downstream DNA fragment. The upstream and downstream DNA fragments were introduced into an amdS-inserted plasmid by using restriction enzymes AflII and KpnI and restriction enzymes MluI and SpeI, respectively, to construct a plasmid for mutation introduction. The plasmid for mutation introduction was then treated with restriction enzymes AflII and SpeI, and the *Trichoderma reesei* QM9414 strain was transformed with the obtained DNA shown by SEQ ID NO: 8 as described in Example 1. The obtained *Trichoderma reesei* mutant strain was used as QM9414 mutant strain II in the following experiments.

Example 4

Protein Production Test Using QM9414 Mutant Strain II

Cultivation was performed by the same operations and conditions as in Example 2 except that QM9414 mutant strain II was used in place of QM9414 mutant strain I prepared in Example 1, and the protein concentration contained in the culture solution and various specific activities of the cellulase were measured. The results are shown in Table 2.

Comparative Example 1

Protein Production Test Using *Trichoderma reesei* QM9414 Strain

Cultivation was performed by the same conditions and operations as in Example 2 except that QM9414 strain was used in place of QM9414 mutant strain I prepared in Example 1, and the protein concentration contained in the culture solution and various specific activities of the cellulase were measured. The results are shown in Table 2.

TABLE 2

| | Comparative Example 1 QM9414 Strain | Example 2 QM9414 Mutant Strain I | Example 4 QM9414 Mutant Strain II |
|---|---|---|---|
| Relative value of protein concentration | 1 | 1.5 | 1.4 |
| Relative value of β-glucosidase specific activity | 1 | 1.3 | 1.5 |
| Relative value of β-xylosidase specific activity | 1 | 1.5 | 1.5 |
| Relative value of cellobiohydrolase specific activity | 1 | 1.4 | 1.3 |

The results of Example 2, Example 4 and Comparative Example 1 revealed that when assuming the protein concentration contained in the culture solution where the *Trichoderma reesei* QM9414 strain was cultivated is 1, the relative value of the protein concentration contained in the culture solution of QM9414 mutant strain I was 1.5 and the relative value of the protein concentration contained in the culture solution of *Trichoderma reesei* QM9414 mutant strain II was 1.4. It is understood from these results that when *Trichoderma reesei* reduced in the function of the polypeptide consisting of the amino acid sequence represented by SEQ ID NO: 2 is cultivated, the protein production amount can be increased, compared to when the function of the polypeptide is not reduced.

With respect to various specific activities of the cellulase, when assuming various specific activities of the cellulase in the culture solution where *Trichoderma reesei* QM9414 strain was cultivated is 1, the β-glucosidase specific activity was QM9414 mutant strain I: 1.3, and QM9414 mutant strain II: 1.4, the β-xylosidase specific activity was *Trichoderma reesei* mutant strain I: 1.5, and QM9414 mutant strain II: 1.5, and the cellobiohydrolase specific activity was QM9414 mutant strain I: 1.4, and QM9414 mutant strain II: 1.3. It is understood from these results that for the cellulase obtained by cultivating *Trichoderma reesei* reduced in the function of the polypeptide consisting of the amino acid sequence represented by SEQ ID NO: 2, not only the amount of protein produced is increased but also there is obtained an unexpected effect that various specific activities of the cellulase are improved, compared to when the function of the polypeptide is not reduced.

Example 5

Saccharification Reaction Test Using Cellulase of QM9414 Mutant Strain II

A saccharification reaction test of a cellulose-containing biomass was performed according to the method described in Reference Example 3 by using a culture solution after 120 hours from the start of cultivation of QM9414 mutant strain II obtained in Example 4. As the cellulose-containing biomass, Arbocel (registered trademark) B800 or a bagasse powder was used. The results are shown in Table 3.

Comparative Example 2

Saccharification Reaction Test Using Cellulase of *Trichoderma reesei* QM9414 Strain A saccharification reaction test of a cellulose-containing biomass was performed by the same operations and conditions as in Example 5 except for using a culture solution after 120 hours from the start of cultivation of *Trichoderma reesei* QM9414 strain obtained in Comparative Example 1. The results are shown in Table 3.

TABLE 3

| | QM9414 Strain | QM9414 Mutant Strain II |
|---|---|---|
| Relative value of glucose concentration (B800 saccharification) | 1 | 1.8 |
| Relative value of glucose concentration (bagasse saccharification) | 1 | 1.8 |

The results of Example 5 and Comparative Example 2 revealed that in the saccharification reaction of Arbocel (registered trademark) B800, when assuming the glucose concentration contained in the saccharified solution using the cellulase of the *Trichoderma reesei* QM9414 strain is 1, the relative value of the glucose concentration in the saccharified solution using the cellulase of QM9414 mutant strain II was 1.8. Furthermore, in the saccharification reaction of bagasse, when assuming the glucose concentration contained in the saccharified solution using the cellulase of

*Trichoderma reesei* QM9414 strain is 1, the relative value of the glucose concentration in the saccharified solution using the cellulase of QM9414 mutant strain II was 1.4. It is understood from these results that when a saccharification reaction of a cellulose-containing biomass is performed using cellulase of the *Trichoderma reesei* reduced in the function of the polypeptide consisting of the amino acid sequence represented by SEQ ID NO: 2, the glucose concentration in the saccharified solution is increased and a larger quantity of sugar can be produced, compared to using cellulase of the *Trichoderma reesei* in which the function of the polypeptide is not reduced.

The invention claimed is:

1. A *Trichoderma reesei* mutant strain wherein an expression of a polypeptide consisting of the amino acid sequence of SEQ ID NO: 2 is reduced.

2. The *Trichoderma reesei* mutant strain according to claim 1, wherein two amino acid residues positioned 347th and 348th in the amino acid sequence of SEQ ID NO: 2 are deleted.

3. A method of producing a protein, the method comprising cultivating the *Trichoderma reesei* mutant strain according to claim 1.

4. A method of producing a protein, the method comprising cultivating the *Trichoderma reesei* mutant strain according to claim 2.

5. A method of producing a cellulase, the method comprising cultivating the *Trichoderma reesei* mutant strain according to claim 1.

6. A method of producing a cellulase, the method comprising cultivating the *Trichoderma reesei* mutant strain according to claim 2.

7. A method of producing a sugar from a cellulose-containing biomass, the method comprising:

producing a cellulase by cultivating a *Trichoderma reesei* mutant strain wherein an expression of a polypeptide consisting of the amino acid sequence of SEQ ID NO:2 is reduced; and saccharifying the biomass with the cellulase in a culture solution.

* * * * *